United States Patent [19]

Käss

[11] Patent Number: 5,898,073
[45] Date of Patent: Apr. 27, 1999

[54] PROCESS FOR THE PREPARATION OF 2,4, 6-TRICHLOROPYRIMIDINE

[75] Inventor: Volker Käss, Leverkusen, Germany

[73] Assignee: Bayer Aktiengesellschaft, Leverkusen, Germany

[21] Appl. No.: 08/984,203

[22] Filed: Dec. 3, 1997

[30] Foreign Application Priority Data

Dec. 10, 1996 [DE] Germany .......................... 196 51 310

[51] Int. Cl.$^6$ ................................................ C07D 239/30
[52] U.S. Cl. ............................................................ 544/334
[58] Field of Search ............................................. 544/334

[56] References Cited

U.S. PATENT DOCUMENTS

| | | | |
|---|---|---|---|
| 3,714,164 | 1/1973 | Steffan | 544/334 |
| 5,525,724 | 6/1996 | Hunds | 544/334 |
| 5,712,394 | 1/1998 | Hansmann et al. | 544/334 |
| 5,719,285 | 2/1998 | Steffan | 544/334 |

FOREIGN PATENT DOCUMENTS

| | | |
|---|---|---|
| 0 101 561 A1 | 2/1984 | European Pat. Off. . |
| 0 101 561 B1 | 2/1984 | European Pat. Off. . |
| 0 697 406 A1 | 2/1996 | European Pat. Off. . |
| 0 747 364 A2 | 12/1996 | European Pat. Off. . |
| 1 933 784 | 1/1971 | Germany . |
| 221 736 A1 | 5/1985 | Germany . |
| 44 08 404 A1 | 9/1995 | Germany . |

OTHER PUBLICATIONS

J. Bradley et al., Journal of the Chemical Society, 1944, London, pp. 678–679.

H. Bredereck et al., Chemische Berichte, vol. 92, 1959, pp. 2937–2943.

*Primary Examiner*—John M. Ford
*Attorney, Agent, or Firm*—Sprung Kramer Schaefer & Briscoe

[57] ABSTRACT

Process for the preparation of 2,4,6-trichloropyrimidine, characterized in that barbituric acid is reacted in a first reaction step with phosphorus oxychloride in the presence or absence of a catalyst, and then, in a second reaction step, is reacted with phosphorus pentachloride or with reactants forming this, in particular phosphorus trichloride and chlorine, at a temperature of 20 to below 80° C.

11 Claims, No Drawings

PROCESS FOR THE PREPARATION OF 2,4,6-TRICHLOROPYRIMIDINE

The present invention relates to a novel process for the preparation of 2,4,6-trichloropyrimidine.

2,4,6-Trichloropyrimidine can be prepared by a process described in Chem. Ber. 92 (1959) 2937, by reacting barbituric acid with phosphorus oxychloride ($POCl_3$) in the presence of dimethylaniline. The resulting 2,4,6-trichloropyrimidine is worked up under aqueous conditions. The yield, based on barbituric acid, is 85% of theory. However, this process is associated with disadvantages. Thus, for example, the aqueous work-up of the reaction mixture containing 2,4,6-trichloropyrimidine is undesirable for an industrial process, since this is problematic for safety reasons and generally a repeated extraction of the aqueous phase is required. In addition, owing to the aqueous work-up, large amounts of wastewater having high phosphate and amine contents are formed. Furthermore, a large amount of the tertiary amine is necessary in the process (about 1.8 mol per mol of barbituric acid), which must be recovered.

If a smaller amount of dimethylaniline is used, as in the process of J. Baddiley et al. J. Chem. Soc. 1944, 678 (about 0.8 mol per mol of barbituric acid), the yield decreases to 59%. If the 2,4,6-trichloropyrimidine is required as an anhydrous starting material for further reactions, subsequent complex dehydration, in which the product partially hydrolyses, cannot be avoided.

A process has been found for the preparation of 2,4,6-trichloropyrimidine which is characterized in that barbituric acid is reacted in a first reaction step with phosphorus oxychloride ($POCl_3$) in the presence or absence of a catalyst, and then, in a second reaction step, is reacted with phosphorus pentachloride ($PCl_5$) or with reactants forming this, in particular phosphorus trichloride ($PCl_3$) and chlorine, at a temperature of 20 to below 80° C.

It is advantageous if the phosphorus oxychloride formed and the unreacted phosphorus oxychloride and the 2,4,6-trichloropyrimidine are then separated off from the reaction mixture, in particular by distillation.

The phosphorus oxychloride separated off in particular by distillation can, for example, be utilized for reuse in the process according to the invention.

Surprisingly, it has been found that the first reaction step proceeds even at low temperatures and without gas formation. The reaction with $POCl_3$ proceeds even at room temperature, but particularly at a temperature of 50 to below 80° C., preferably from 60 to 75° C. At higher temperatures, although the 1st reaction step proceeds slightly quicker, it generally leads, even after a short time, to tough insoluble precipitates of polyphosphorus compounds. This solidifying of the reaction mixture prevents an industrial procedure in particular.

In a preferred embodiment of the process according to the invention, the 1st reaction step proceeds without HCl formation. Particular preference is given to the additional introduction of HCl in an amount of 1 to 6 mol per mol of barbituric acid. The HCl used for this can, for example, be taken off from the 2nd reaction step in which it is formed.

The 2nd reaction step is likewise carried out at a temperature of 20 to below 80° C., preferably at 60 to below 80° C., in particular at 60 to 75° C.

The phosphorus oxychloride is preferably used in an amount of 3 to 15 mol, in particular 4 to 7 mol, based on 1 mol of barbituric acid.

Although amounts of phosphorus oxychloride greater than 15 mol, based on 1 mol of barbituric acid, can be used, they do not offer any particular advantage. Amounts smaller than the 3 mol per mol of barbituric acid required for the complete reaction lead to lower yields and may lead to unstirrable reaction mixtures.

Phosphorus oxychloride preferably adopts the function of a solvent, so that the process according to the invention can preferably be carried out without additional solvents.

However, the respective reaction steps can also proceed in the presence of an inert solvent. It is likewise advantageous to carry out the process in the absence of water. The hydrogen chloride which may be formed in the first reaction step and which is formed in the second reaction step escapes and can be removed from the exhaust air using a scrubber, for example.

For the catalyst optionally present in the first reaction step, organic bases, for example, are suitable, such as tertiary amines, for example triethylamine, tripropylamine, tri-n-butylamine, dimethylaniline, diethylaniline, N,N-diethylmethylaniline, N-ethyl-diisopropylamine, trioctylamine, triisobutylamine, 1,8-bis(dimethylamino)-naphthalene, N,N-dimethyl-p-toluidine or similar compounds, in addition N-substituted carboxamides and sulphonamides or N,N-disubstituted carboxamides and sulphonamides, such as N,N-dimethylformamide, N,N-diethylformamide, N,N-dimethylacetamide, N,N-diethylacetamide, N-formylpiperidine, tetramethylurea, 1-alkyl-2-pyrrolidones, such as, for example, 1-methyl-2-pyrrolidone (NMP), 1-octyl-2-pyrrolidone or 1-dodecyl-2-pyrrolidone, dibutylformamide and methylstearylformamide and basic heterocycles, such as pyridine, 2-methylpyridine, 3-methylpyridine, 4-methylpyridine, 2-ethylpyridine, 4-ethylpyridine, 2,4-dimethylpyridine, 2,6-dimethylpyridine, 3,5-dimethylpyridine, 5-ethyl-2-methylpyridine, 2,4,6-trimethylpyridine, 4-(dimethylamino)-pyridine, 4-(1-pyrolidinyl)-pyridine and quinoline; obviously, mixtures of the said catalysts can also be used.

Optionally used catalysts are preferably used in an amount of less than 0.1 mol, in particular less than 0.03 mol, per mol of barbituric acid, amounts greater than 0.1 mol per mol of barbituric acid not offering any particular advantage.

In the second reaction step, the reaction is preferably carried out with 2.0 to 5 mol of phosphorus pentachloride or reactants forming this, in particular with 3.0 to 3.3 mol of phosphorus trichloride and 2.4 to 3.5, in particular 2.9 to 3.2, mol of chlorine per mol of barbituric acid. The reaction of the process according to the invention proceeds expediently, in particular, if phosphorus trichloride and chlorine are used in stoichiometric amounts; i.e. 3 mol of chlorine and 3 mol of phosphorus trichloride are used per mol of barbituric acid. It is advantageous to add the phosphorus trichloride wholly or partly, before, or simultaneously with, the chlorine. Preferably, phosphorus trichloride and chlorine are added to the reaction mixture simultaneously. Chlorine gas in this case is preferably introduced directly into the reaction mixture through a gas-entry tube. It is particularly advantageous if no chlorine excess occurs during the reaction. Although an excess of chlorine is possible, it offers no particular advantages, but, in contrast, leads to greater complexity in exhaust gas disposal. A slight excess of $PCl_3$ is advantageous. A marked $PCl_3$ excess does not interfere with the actual reaction of the second reaction step, but the higher $PCl_3$ contents in the $POCl_3$ resulting therefrom may be disadvantageous when $POCl_3$ is used again for a further reaction vessel. The $POCl_3$ recovered by distillation preferably has a $PCl_3$ content of <5%, in particular <1%. Although a $PCl_5$ excess is possible, it generally leads, owing to sublimation during product distillation, to undesirable deposits in the distillation column and in the exhaust gas system.

The yield of 2,4,6-trichloropyrimidine which is obtained by the process according to the invention is generally 90 to 94% of theory, based on barbituric acid. The resulting 2,4,6-trichloropyrimidine is essentially free from 2,4,5,6-tetrachloropyrimidine and from water. No chlorination in the 5 position of the pyrimidine was observed under the process conditions according to the invention. The process according to the invention offers several advantages in comparison with the processes known hitherto. In addition to a higher yield, the 2,4,6-trichloropyrimidine is obtainable in a highly pure form from the reaction mixture by distillation in a technically extremely simple manner. In addition, with a preferably nonaqueous work-up, wastewater is not even produced.

The product produced by the process according to the invention can be obtained from the reaction mixture by distillation, for example. 2,4,6-Trichloropyrimidine isolated in this manner may contain up to 1% of phosphorus compounds. If particularly high purities are required, for example for the preparation of plant protection products, it is advantageous firstly to free the resulting reaction mixture from $POCl_3$ by distillation, and then to heat it at a temperature of about 170° C., preferably for about 2 hours.

The product then obtained by distillation has a high purity.

The heating can be carried out for different periods at various temperatures, for example for 2 to 4 hours at 150 to 170° C. or for 4 to 6 hours at 130 to 150° C.

2,4,6-Trichloropyrimidine is known as an important intermediate for the preparation of reactive dyes and active ingredients for plant protection and as a starting product for the preparation of other important pyrimidine derivatives, such as 2,4,6-trifluoropyrimidine.

EXAMPLES

Example 1

520 kg (4.06 mol) of barbituric acid and 10 kg of N-methylpyrrolidone were added to 3500 kg (32.2 mol) of phosphorus oxychloride introduced in advance, and the mixture was then heated to 75+/−5° C. No gas formation was observable at this temperature, and the batch also remained a suspension. After a further stirring time of 7 hours, 1675 kg (12.2 kmol) of phosphorus trichloride were added and 850 kg (12.1 kmol) of chlorine were introduced at 75+/−5° C. Vigorous gas formation took place. After completion of chlorination, phosphorus oxychloride (4815 kg) was distilled off at atmospheric pressure. After addition of a ditolyl ether mixture as a distillation aid, a $POCl_3$-2,4,6-trichloropyrimidine fraction (270 kg) was distilled off, which can be reused in the next batch. 2,4,6-Trichloropyrimidine was then distilled under reduced pressure. Yield: 685 kg of 2,4,6-trichloropyrimidine, corresponding to approximately 93% of theory.

Example 2

Simultaneous addition 512 g (4 mol) of barbituric acid and 10 g of N-methylpyrrolidone were added to 3500 g (23,2 mol) of phosphorus oxychloride introduced in advance, and the mixture was then heated to 75+/−5° C. After a further stirring time of 7 hours, 1650 g (12.0 mol) of phosphorus trichloride and 840 g (11.8 mol) of chlorine were added and introduced simultaneously. After work-up by distillation, 661 g of 2,4,6trichloropyrimidine were obtained, corresponding to a yield of 90% of theory.

Example 3

Heating prior to product distillation 512 g (4 mol) of barbituric acid and 10 g of N-methylpyrrolidone were added to 3500 g of phosphorus oxychloride introduced in advance, and the mixture was then heated to 75+/−5° C. After 7 hours, 1650 g of phosphorus trichloride were added and chlorine was introduced at 75+/−5° C. After completion of chlorination, phosphorus oxychloride was distilled off at atmospheric pressure and, after addition of a distillation aid, a $POCl_3$-2,4,6-trichloropyrimidine fraction was distilled off under reduced pressure. After venting, the distillation residue was stirred for 2 hours at 170° C. Then the $POCl_3$ newly formed during the heating was first distilled off, and after this 2,4,6-trichloropyrimidine was distilled off, under reduced pressure. Yield: 673 g of 2,4,6-trichloropyrimidine distilled off, corresponding to approximately 91.7% of theory. The product obtained in this manner is particularly pure (content 99.8%) and contains phosphorus compounds only in traces.

Example 4

Addition of HCl gas 512 g (4 mol) of barbituric acid and 10 g of triethylamine were added to 3500 g (23.2 mol) of phosphorus oxychloride introduced in advance, and the mixture was then heated to 75+/−5° C. 182 g of hydrogen chloride were introduced at this temperature. 1650 g of phosphorus trichloride were then added and 840 g of chlorine introduced. After work-up by distillation, 668 g of 2,4,6-trichloropyrimidine were obtained, corresponding to approximately 91.0% of theory.

I claim:

1. A process for the preparation of 2,4,6-trichloropyrimidine, wherein barbituric acid is reacted in a first reaction step with phosphorus oxychloride in the presence or absence of a catalyst, and then, in a second reaction step, is reacted with phosphorus pentachloride or with reactants forming this, at a temperature of 20 to below 80° C.

2. The process for the preparation of 2,4,6-trichloropyrimidine, according to claim 1, wherein phosphorus trichloride and chlorine are applied as reactants for forming phosphorus pentachloride in the second reaction step.

3. The process according to claim 1, wherein the first reaction step is carried out at a temperature of 50 to below 80° C., and the second reaction step is carried out at a temperature of 60 to below 80° C.

4. The process according to claim 1, wherein the first reaction step is carried out at a temperature from 60 to 75° C., and the second reaction step is carried out at a temperature of 60 to 75° C.

5. The process according to claim 1, wherein in the second reaction step, the phosphorus trichloride is added wholly or partly before, or simultaneously with, the chlorine.

6. The process according to claim 5, wherein for the reaction of the second reaction step, phosphorus trichloride and chlorine are added to the reaction mixture simultaneously.

7. The process according to claim 1, wherein as catalyst, use is made of tertiary amines, N-substituted carboxamides and sulphonamides or N,N-disubstituted carboxamides and sulphonamides, or basic heterocycles.

8. Process according to claim 1, wherein as catalyst, use is made of triethylamine, tributylamine, N,N-dimethylformamide or 1-methyl-2-pyrrolidone.

9. The process according to claim 1, wherein 2.5 to 5 mol, of phosphorus trichloride and 2.4 to 3.5 mol, of chlorine are used per mol of barbituric acid.

10. The process according to claim 1, wherein 3.0 to 3.3 mol, of phosphorus trichloride and 2.9 to 3.2 mol, of chlorine are used per mol of barbituric acid.

11. The process according to claim 1, wherein HCl is introduced in the first reaction step.

* * * * *